United States Patent
Cribbs et al.

(10) Patent No.: US 7,841,984 B2
(45) Date of Patent: *Nov. 30, 2010

(54) ULTRASONIC TREATMENT AND IMAGING OF ADIPOSE TISSUE

(75) Inventors: Robert Cribbs, Placerville, CA (US); Carl Hennige, Folsom, CA (US); Rick Hillstead, Duluth, GA (US)

(73) Assignee: Medicis Technologies Corporation, Bothell, WA (US)

( * ) Notice: Subject to any disclaimer, the term of this patent is extended or adjusted under 35 U.S.C. 154(b) by 194 days.

This patent is subject to a terminal disclaimer.

(21) Appl. No.: 11/776,436

(22) Filed: Jul. 11, 2007

(65) Prior Publication Data

US 2008/0015435 A1   Jan. 17, 2008

Related U.S. Application Data

(62) Division of application No. 10/371,973, filed on Feb. 20, 2003, now Pat. No. 7,258,674.

(60) Provisional application No. 60/357,628, filed on Feb. 20, 2002.

(51) Int. Cl.
*A61B 8/00* (2006.01)

(52) U.S. Cl. .............. 600/437; 600/438; 600/463; 601/2

(58) Field of Classification Search .......... 600/437, 600/438, 463; 601/2
See application file for complete search history.

(56) References Cited

U.S. PATENT DOCUMENTS

| | | | |
|---|---|---|---|
| 3,622,958 A * | 11/1971 | Tucker et al. ............ | 367/92 |
| 4,397,314 A | 8/1983 | Vaguine | |
| 4,441,486 A | 4/1984 | Pounds | |
| 4,527,550 A | 7/1985 | Ruggera et al. | |
| 4,601,296 A | 7/1986 | Yerushalmi | |
| 4,763,525 A * | 8/1988 | Cobb ......................... | 73/599 |
| 5,143,063 A | 9/1992 | Fellner | |
| 5,419,761 A | 5/1995 | Narayanan et al. | |
| 5,676,692 A | 10/1997 | Sanghvi et al. | |
| 5,735,280 A | 4/1998 | Sherman et al. | |

(Continued)

FOREIGN PATENT DOCUMENTS

DE    2508494    9/1976

(Continued)

OTHER PUBLICATIONS

Cleveland et al. "A Dual Passive Cavitation Detector for Localized Detection of Lithotripsy-Induced Cavitation In Vitro." Mar. 2000. J. Acoust Soc. Am., 107 (3), pp. 1745-1758.*

(Continued)

*Primary Examiner*—Brian Casler
*Assistant Examiner*—James Kish
(74) *Attorney, Agent, or Firm*—Townsend and Townsend and Crew LLP

(57) ABSTRACT

A system for imaging tissue during ultrasound therapy treatments is described. The system has a high intensity focused ultrasound transducer, video display and controller. The controller has two receive paths for detecting cavitation and boiling in present during an ultrasound therapy treatment, and representing the two visually on a display.

1 Claim, 13 Drawing Sheets

U.S. PATENT DOCUMENTS

| | | | |
|---|---|---|---|
| 5,749,364 A | 5/1998 | Sliwa, Jr. et al. | |
| 5,827,204 A * | 10/1998 | Grandia et al. | 601/2 |
| 5,873,828 A | 2/1999 | Fujio et al. | |
| 5,879,303 A | 3/1999 | Averkiou et al. | |
| 6,007,499 A * | 12/1999 | Martin et al. | 601/3 |
| 6,042,556 A | 3/2000 | Beach et al. | |
| 6,071,239 A | 6/2000 | Cribbs et al. | |
| 6,086,535 A | 7/2000 | Ishibashi et al. | |
| 6,315,741 B1 | 11/2001 | Martin et al. | |
| 6,325,769 B1 | 12/2001 | Klopotek | |
| 6,405,072 B1 | 6/2002 | Cosman | |
| 6,413,216 B1 | 7/2002 | Cain et al. | |
| 6,432,067 B1 | 8/2002 | Martin et al. | |
| 6,500,141 B1 | 12/2002 | Irion et al. | |
| 6,508,774 B1 * | 1/2003 | Acker et al. | 601/2 |
| 6,524,250 B1 | 2/2003 | Weber et al. | |
| 6,572,839 B2 | 6/2003 | Sugita et al. | |
| 6,599,256 B1 | 7/2003 | Acker et al. | |
| 6,692,438 B2 | 2/2004 | Skyba et al. | |
| 6,719,449 B1 | 4/2004 | Laugharn, Jr. et al. | |
| 6,875,176 B2 | 4/2005 | Mourad et al. | |
| 7,165,451 B1 | 1/2007 | Brooks et al. | |
| 2003/0018255 A1 | 1/2003 | Martin et al. | |
| 2003/0130599 A1 * | 7/2003 | Restle et al. | 601/2 |
| 2004/0030227 A1 | 2/2004 | Littrup et al. | |

FOREIGN PATENT DOCUMENTS

| | | |
|---|---|---|
| DE | 19800416 A1 | 7/1999 |
| GB | 2 279 742 A | 6/1993 |
| WO | WO 01/87161 | 11/2001 |

OTHER PUBLICATIONS

Fritzsche (1986). "With FDA Approval and Reimbursement in Place, Hyperthermia is Fourth Major Anti-Cancer Weapon," The Medical Business Journal, 80-82.

Sapzhinkov et al., "Ultrasound-guided localized detection of cavitation during lithotripsy in pig kidney in vivo," Proc IEEE Ultrasonics Symp 2001;1347-1350.

Zhong et al., "Inertial cavitation and associated acoustic emission produced during electrohydraulic shock wave therapy," Journal of the Acoustic Society of America, May 1997; 101(5):2940-2950.

Supplementary European Search Report of EP Patent Application No. 03716122.1, mailed May 7, 2010, 7 pages total.

* cited by examiner

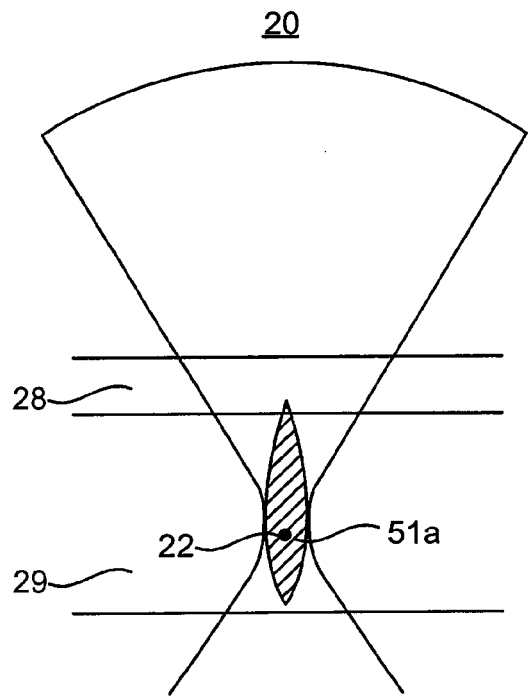
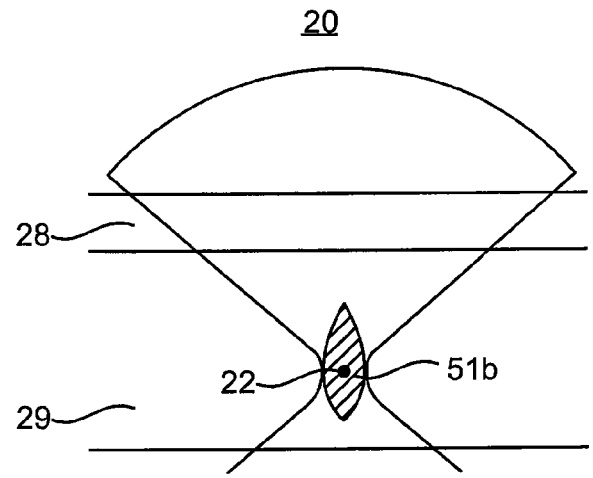
FIG. 5A            FIG. 5B
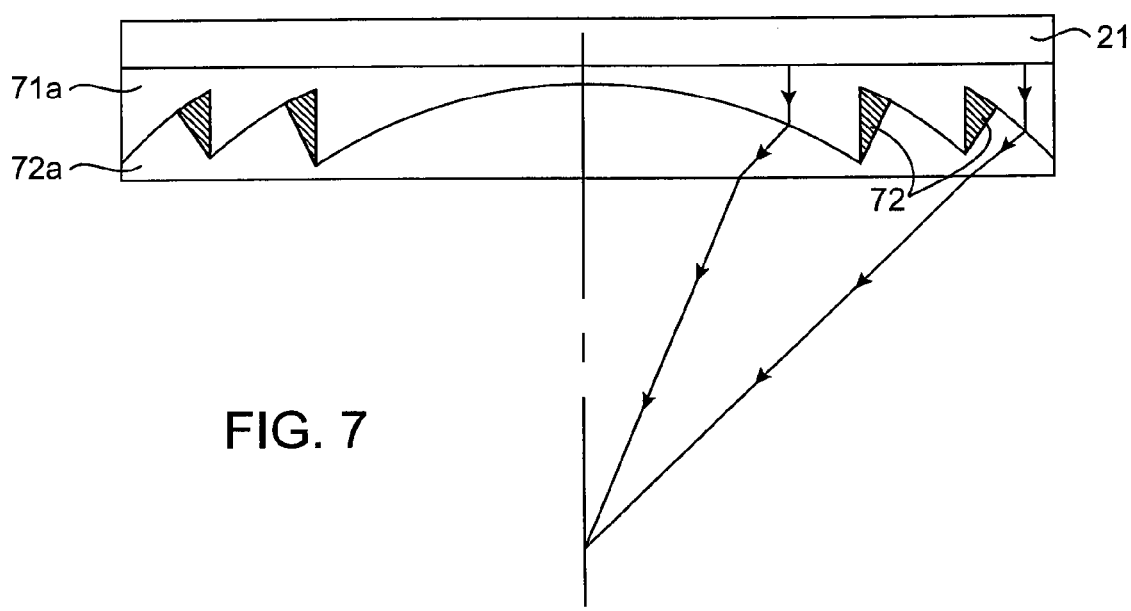
FIG. 7

ULTRASONIC TREATMENT AND IMAGING OF ADIPOSE TISSUE

CROSS-REFERENCES TO RELATED APPLICATIONS

The present application is divisional of U.S. patent application Ser. No. 10/371,973 which claimed priority from U.S. Patent Application Ser. No. 60/357,628, filed Feb. 20, 2002, the full disclosures of which are incorporated herein by reference.

BACKGROUND OF THE INVENTION

1. Field of the Invention

The present invention relates to a method and apparatus for ablating human fat by ultrasonically destroying cells.

2. Description of the Background Art

Adipose tissue, more commonly known as "fat," is formed of cells containing stored lipid. Fat cells are very large, ranging up to 120 microns in diameter. They are typically spherical, but may assume polyhedral shapes because of mutual deformation. A single droplet of lipid occupies most of the volume of the cell. The nucleus of the cell is displaced to one side by the accumulated lipid and the cytoplasm is reduced to a thin rim comprising only about one fortieth of the total volume of the cell. Each cell is surrounded by delicate reticular fibers. Capillaries are found in the angular spaces between the cells. Capillaries form a loose plexus throughout the adipose tissue. Adipose tissue appears in section as a delicate network with large polygonal meshes.

Adipose tissue is often subdivided into small lobules by connective tissue septa. This compartmentalization, visible with the naked eye, is most obvious in regions where the fat is subjected to pressure. In other regions, the connective tissue septa are thinner and the lobular organization of the tissue is less apparent.

Adipose tissue is widely distributed in the subcutaneous tissue, but exhibits regional differences in amount. Those regional differences are influenced by age and sex. In infants and young children there is a continuous subcutaneous layer of fat, the panniculus adiposus has a rather uniform thickness over the whole body. In adults the panniculus adiposus thins out in some regions but persists and grows thicker in certain sites of predilection. These sites differ in the two sexes and are largely responsible for the characteristic differences in body form of males and females. In the male, the principal areas are the neck and the region overlying the seventh cervical vertebra, the subcutaneous area overlying the deltoid and triceps, the lumbrosacral region, and the buttocks. In the female, subcutaneous fat is most abundant in the anterior neck, the breasts, the buttocks, the epitrochanteric region, and the anterior aspect of the thigh. Few blood vessels pass through subcutaneous fat into the overlying skin, which receives its nutrients through a subdermal plexus of blood vessels that run above the fatty layer.

In addition to the aforementioned fat deposits, there are extensive accumulations in both the sexes in the omentum, mesenteries, and retroperitoneal areas. All of the aforementioned areas readily give up their stored lipid during fasting. There are other areas of fat, however, that do not give up their stored fuel so readily. For example, the adipose tissue in the orbit, in the major joints, and on the palms of the hands and soles of the feet does not seem to be grist for the metabolic mill, but instead has the mechanical function of support or protection. These areas diminish in size only after very prolonged starvation.

An excess of adipose tissue, i.e., obesity, may be unhealthful because it gives rise to varying health problems in human beings, both physical and psychological in nature. Beyond psychological effects such as poor self-image, obesity typically increases the risk of conditions such as heart disease, high blood pressure, osteoarthritis, bronchitis, hypertension, diabetes, deep-vein thrombosis, pulmonary emboli, varicose veins, gallstones and hernias.

Thus, there is a clear need for methods capable of removing fatty tissue. Dieting or learning good eating habits are effective to a degree but are not long-range solutions for most people; nor are these approaches effective in situations where undesirable fatty deposits are localized in the body.

Liposuction extracts adipose tissue from the body by purely mechanical means. If fat cells are destroyed after puberty, the remaining fat cells will attempt to compensate to some degree, but about 70% of the fat contained in the destroyed cells is never recovered by the body. The permanent removal of fat from the human body is a highly desirable but very difficult undertaking. Liposuction, however, is a highly invasive and potentially disfiguring procedure associated with a prolonged and uncomfortable recovery due to the resulting separation of the skin from the body. For that reason, liposuction is not practical for weight control therapy, but may be practical body reshaping only in limited areas.

Electromedical methods and apparatus have been used in the past for various surgical and therapeutic procedures. For example, U.S. Pat. No. 4,527,550 to Ruggera et al., discloses a radio frequency diathermy apparatus including means for localizing the heat focus. U.S. Pat. No. 4,397,313 to Vaguine discloses a microwave hyperthermia apparatus including means for producing a concave electric field for focusing the electromagnetic energy at a particular region of the body. Federal Republic of Germany Patent 2,508,494 to Schultz, U.S. Pat. No. 4,343,301 to Indech, and U.S. Pat. No. 3,958,559 to Glenn et al., relate to ultrasound devices that can be focused on a tumor, for example, within the body.

However, these aforementioned systems have not been used for removal of fatty tissue. In fact, some systems recognize the need to avoid damage to adipose or other tissue surrounding the tissue to be destroyed. See, e.g., U.S. Pat. No. 3,958,559 at col. 1, lines 24-25; U.S. Pat. No. 4,397,313 at col. 2, lines 45-57. See also U.S. Pat. No. 4,601,296 to Yerushalmi, which notes at col. 1, lines 30-46 that known devices are capable of automatically controlling the undesired RF heating of healthy tissue. These devices monitor the temperature adjacent the work site, and responsively control the operation of the antenna and of a cooling system.

U.S. Pat. No. 4,397,314 to Vaguine, points out at col. 1, line 54-col. 2, line 11, that healthy tissues are heated by prior art hyperthermia systems less effectively than tumors, since healthy tissue is characterized by a developed blood vessel network and a normal vasodilation response to heat, whereby blood flow may increase threefold after five minutes of heating, for example. On the other hand, tumors are characterized by a damaged blood vessel network and a blood flow that collapses during heating.

U.S. Pat. No. 4,441,486 to Pounds relates to ultrasound hyperthermia. This patent acknowledges the need to control the coverage of the hyperthermia treatment, but points out that with ultrasound this is not a great problem, since ultrasound does not preferentially heat fatty tissue.

U.S. Pat. No. 5,143,063 to Fellner is understood to relate to treatments of adipose tissue using ultrasound energy, or alternatively, microwave or radio frequency waves. The patent does not, however, discuss imaging techniques that ensure treatment regions are covered by the treatment energy.

U.S. Pat. No. 6,071,239 to Cribbs is understood to teach a HIFU array used in a method of selectively destroying fat cells. The patent, however, does not reasonably teach tracking and imaging the progression of the treatment zones.

According to Fritzsche, "With FDA Approval and Reimbursement in Place, Hyperthermia is Fourth Major Anti-cancer Weapon," The Medical Business Journal, March 1986, at 80-82, one capacitive RF hyperthermia device manufactured by Yamamoto in Japan is effective only where there is a low percentage of body fat.

The disclosures of the above-referenced patents and materials are incorporated by reference herein.

Thus, there is a recognition by the art that adipose tissue should not be heated inadvertently during hyperthermia, and a further recognition that adipose tissue, being more effectively blood-cooled than tumor tissue, is inherently unlikely to inadvertently receive a damaging energy dosage during hyperthermia treatment by means of the prior art systems intended for treatments of tumors or the like.

BRIEF SUMMARY OF THE INVENTION

Accordingly, the present invention is directed to ultrasonic treatment and imaging of adipose tissue in a manner that substantially obviates one or more of the problems due to limitations and disadvantages of the related art.

The present invention relates to a system for the destruction of adipose tissue utilizing high intensity focused ultrasound (HIFU) within a patient's body, the system comprising: a controller for the electronic storage of data and for controlling a plurality of system components; a means for mapping a human body to establish three dimensional coordinate position data for existing adipose tissue within said human, wherein said controller is able to identify a plurality of adipose tissue locations on said human body and establish a protocol for adipose tissue destruction; a transducer assembly having one or more piezoelectric element(s) for emitting high intensity focused ultrasound, and at least one sensor wherein said sensor provides feed back information to said controller for the safe operation of the one or more piezoelectric element(s); wherein said at least one sensor is electronically coupled to said controller, and said controller provides essential treatment command information to said one or more piezoelectric element(s) based on positioning information obtained from said three dimensional coordinate position data.

An advantage of the present invention is to provide a data collection system having a probe and a linear array ultrasonic imaging system. A linear array optical camera is coupled to the skin through a fiber optic faceplate. The linear array is comprised of a plurality of full color pixels. As the optical camera is scanned, the data collection system maps an image or "fingerprint" of the skin. The fingerprint is used as a coordinate system for future data collection and treatment.

Another advantage of the present invention is to provide a transducer prove that integrates into a laser "mouse"-type system that tracks the motion of the transducer. At each end of the transducer probe are optical sensors. It will thus be able to sense not only motion, but also rotation of the assembly.

Another advantage of the present invention provides probes within a transducer that measure boiling and cavitation of adipose tissue, as well as fat thickness.

Another advantage of the present invention is that it provides the practitioner with a skin "fingerprint" detailing the treatment regions of the body.

Additional features and advantages of the invention will be set forth in the description which follows, and in part will be apparent from the description, or may be learned by practice of the invention. The objects and other advantages of the invention will be realized and attained by the structure particularly pointed out in the written description and claims hereof as well as the appended drawings.

To achieve these and other advantages and in accordance with the purpose of the present invention, as embodied and broadly described, a high intensity focused ultrasound transducer comprised of a plurality of piezoelectric elements, a Fresnel type lens coupled to the piezoelectric elements, wherein the Fresnel type lens comprises at least two materials, and wherein the transducer further comprises a plurality of sensors that measure any cavitation, boiling and/or the thickness of a fat layer.

It is to be understood that both the foregoing general description and the following detailed description are exemplary and explanatory and are intended to provide further explanation of the invention as claimed.

BRIEF DESCRIPTION OF THE DRAWINGS

FIGS. 5A and 5B illustrate relationships between the tissue kill zone and focal length of a transducer element;

FIGS. 7 and 8 illustrate a Fresnel lense in accordance with the principles of the present invention;

DETAILED DESCRIPTION OF THE INVENTION

As above noted, it is beneficial to eliminate some (or some major part) of the subcutaneous adipose tissue for both cosmetic and fundamental health reasons. To this end, in accordance with the principles of the present invention, upon consultation with a patient, a practitioner sets up a treatment plan. That treatment plan includes determining the thickness of fat in the areas where fat is to be removed from within the body.

Then, the optimum locations for the removal of fat is automatically determined. Generally, fat located at the deepest levels within the body is removed first.

The practitioner then reviews the data and verifies that the fat layer is properly identified.

The treatment plan is then stored in a computer and the practitioner applies a transducer capable of creating high intensity focused ultrasound (HIFU) beams to the patient.

The practitioner then "paints" the region to be treated using a display that includes a map of the treatment region. For example, a display might show red over a blue background where, as an area becomes treated, red changes to yellow. The computer tracks the treated areas to prevent overexposure to HIFU beams and to prevent multiple ensonifications. It is not necessary for the practitioner to pain in any particular pattern. All that is required is to completely "paint" the region of interest. A combination of sensors on the transducer are used to identify overlapping regions and to prevent damage. The practitioner continues painting until no more red areas exist on the display, indicating that treatment is complete.

Reference will now be made in detail to the accompanying drawings.

In order to develop a treatment plan, the patients' body is first mapped with a mapping device. The mapping device produces an ultra high resolution "photograph" of the skin over a treatment region. The photograph enables treatment and records to be kept and correlated over multiple visits.

The mapping system locates imperfections in the skin, i.e., crevices, freckles, hair follicle patterns, etc., to be used to key all subsequent measurements and treatments. The location of the imperfections are determined from a high resolution color image. That high resolution image has a higher resolution than standard high-resolution video.

Figure 1:
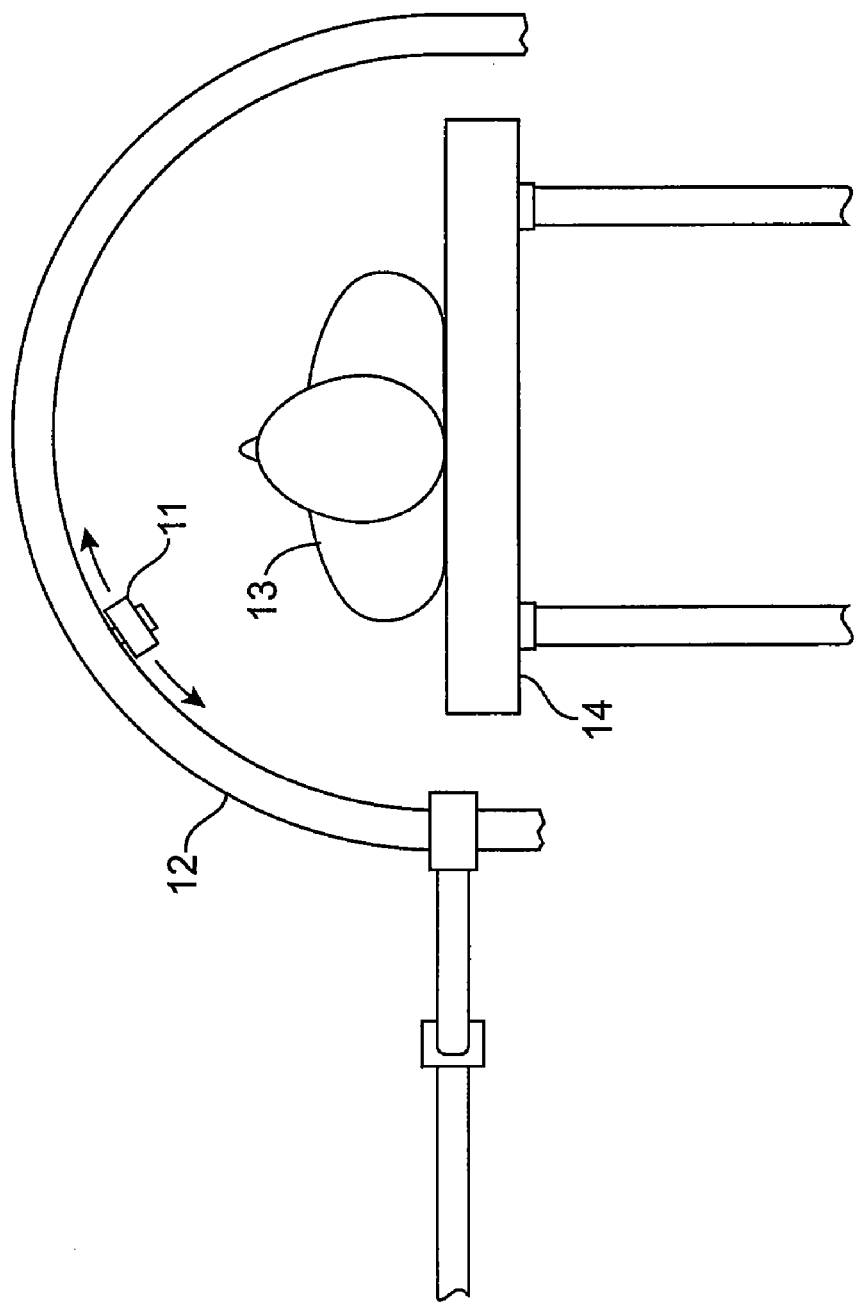
FIG. 1 illustrates a mapping system in accordance with the principles of the present invention.

A mapping system, as illustrated in FIG. 1, comprises a line scan camera 11. The line scan camera images only along a line and has a very high resolution, e.g., 4,096 pixels. The line scan camera is attached to a track 12 that extends over the patient. The track may be a type of gantry for the line scan camera, and other elements of the mapping system to traverse during use. The line scan camera 11 is therefore capable of orbiting patient 13 lying on table 14. During the mapping process, the patient lies on the patients' back and then the patients' stomach. By sequentially scanning the patient lying on his back and stomach using the line scan camera 11 on the track 12, two images may be made. For example, if the region scanned were 18 inches with 4,000 pixels, then each pixel represents 5 mils (200 lines/inch). In some embodiments the image may be 6,000 pixels long.

Once the body is mapped, the practitioner examines the region of the skin where fat is to be removed during an assessment step by scanning the body with a high-resolution linear array ultrasound system. The linear array ultrasonic system operates at approximately 7.5 MHz and measures fat thickness on a body. The fat thickness measurements allow the practitioner to mark contours of constant fat thickness onto the skin.

More specifically, the practitioner scans treatment regions of body and marks dots onto the locations of the skin delineating underlying fat deposits 0.5, 1.0, 1.5, 2.0, 2.5, . . . cm thick, wherein each fat thickness is identified with a different color of ink. Connecting dots of the like color provides the contours of constant fat thickness. At this point the body is imaged.

After the patient has been imaged, a printer prints a long, high-resolution paper, herein referred to as a skin fingerprint, containing the contours of constant fat thickness. The skin fingerprint would look like the skin laid flat. This becomes a working document.

The practitioner then traces the contours of the treatment using a pen that writes in ink and electronically enters coordinates of the contours into a computer record.

A final skin fingerprint, containing final constant fat contours, consistent with the target body shape, is then made. A graph supplied to the practitioner shows a minimum final fat thickness allowed versus the measured thickness at the beginning of the treatment plan. The final set of contours representing a target shape of the patient's body do not violate information from the graph. The second set of contours are then entered into the computer with an electronic pencil over the print. The computer then prints a treatment plan comprising a sequence of skin fingerprints showing contours and HIFU transducers to be used during each session, consistent with the target shape and a maximum volume of fat that may be removed per session. The treatment plan is therefore defined in terms of contours of treatment for transducers of various focal lengths at predetermined treatment intervals. The treatment plan is also consistent with a desired symmetry, the removal of deep fat before superficial fat, and a minimum amount of fat required over the body.

Once a treatment plan is determined, treatment of the patient begins. The treatment device comprises a HIFU system—in particular, a system with a plurality of independently controlled multiple beam transducer elements that are capable of being focused at the treatment depths below the skin surface.

Figure 2:
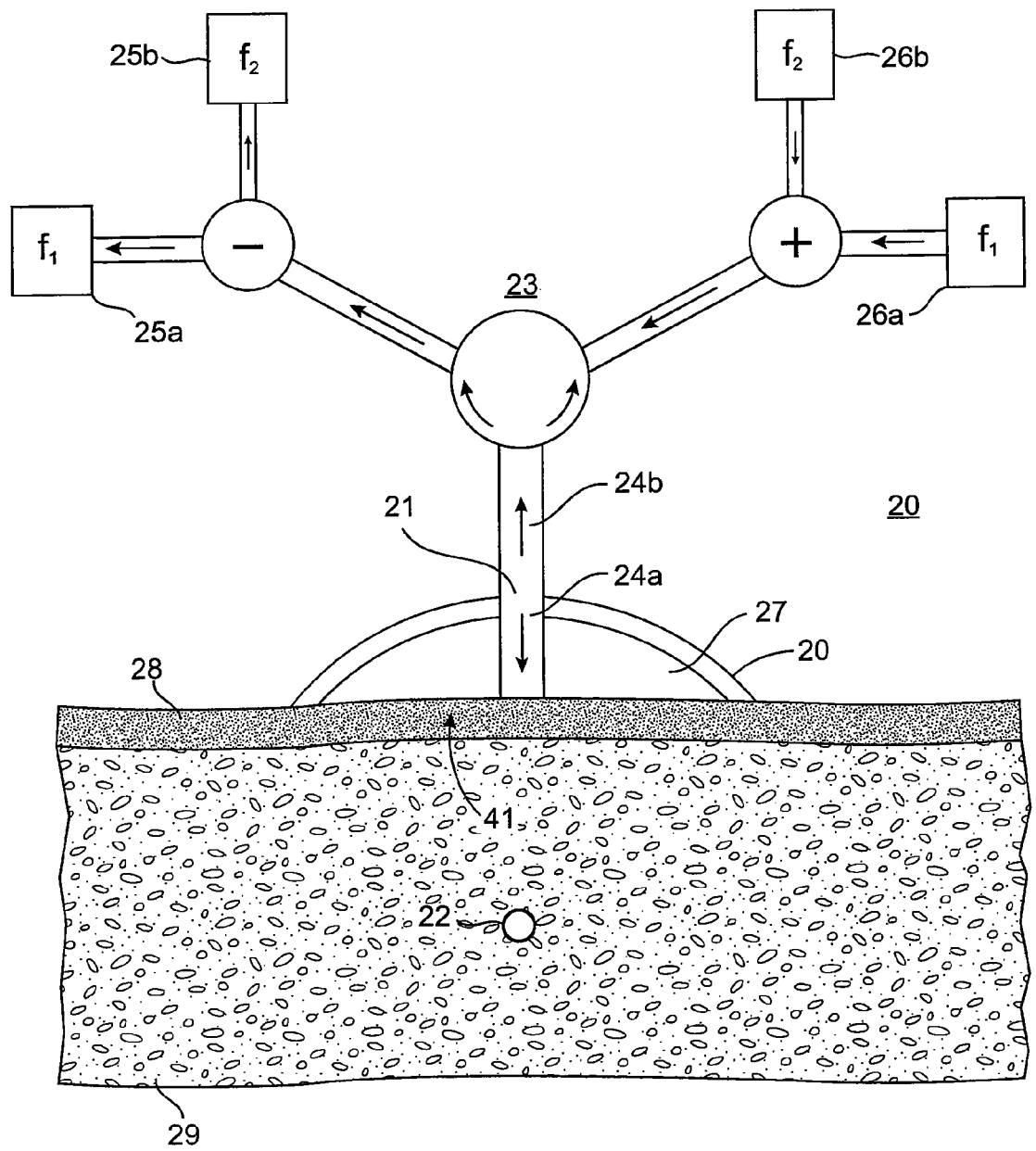
FIG. 2 illustrates a schematic view of a representative transducer element including an optical system according to one aspect of the present invention.
Figure 3:
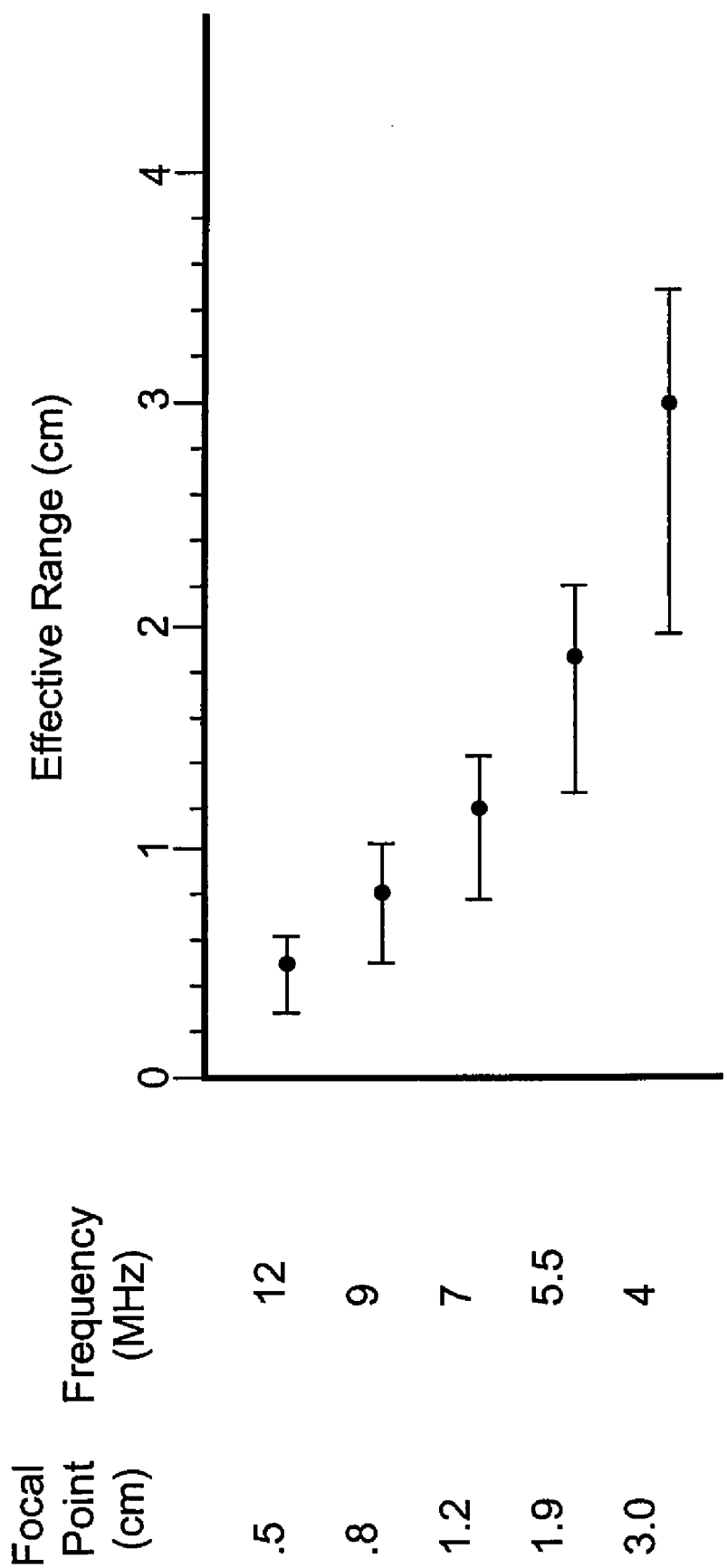
FIG. 3 illustrates the transducer depths of transducer elements having different focal points and using different frequencies used according to the present invention.

The treatment begins by applying a HIFU transducer, comprised of an array of transducer elements, to the patient. Referring to FIG. 2, each transducer element 20 comprises a piezoelectric element 21, solid coupling element 27, air cooling (not shown), and focusing lens (not shown). In an exemplary embodiment of the present invention, and referring now to FIG. 3, five transducer elements span treatment depths including 0.35 to 3.5 cm. The five transducer elements have focal points of 0.5, 0.8, 1.2, 1.9, and 3.0 cm, with correspondingly operate frequencies of 12, 9, 7, 5.5, and 4 MHz, respectively. It should be noted that the transducer may comprise different numbers of transducer elements.

Figure 4A:
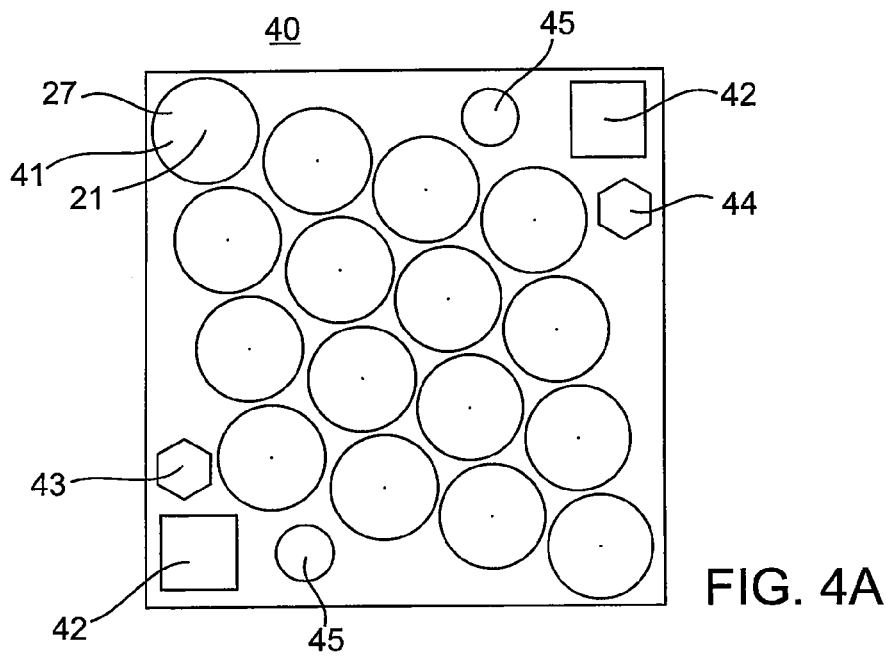
FIG. 4A-C illustrates a bottom view of representative transducers that are in accord with the principles of the present invention.

FIG. 4A shows a bottom view of a 1.2 cm focal length transducer 40. In another exemplary embodiment, the transducer comprises 16 transducer elements 41 that are staggered to create 16 beam paths 141 that are spaced 0.3 cm apart. The beams may be operated in two modes: a first mode that creates a hexagonal pattern of destroying tissue (as viewed from the top); and a second mode that creates a continuous path of destroyed tissue. It should be noted, however, that the transducer may comprise different numbers of transducer elements. A single piezoelectric element can be used for the generation of the HIFU, or an array style transducer.

In one aspect of the present invention, the HIFU transducer may comprise a plurality of independently movable HIFU transducer elements assembled in a matrix. Accordingly, each individual transducer element may be moved with an "orbital" type motion, much like motion restricted to that of a "ball and socket" joint. This orbital type motion allows the focal point of ablation to describe a circular region in the tissue, thus applying energy to more tissue than would be delivered if the individual transducers were fixed and immobile. Circles of treated tissue created by this motion may overlap one another or may be sized so as to not overlap. In one aspect of the invention, the transducer elements may be positioned and operated such that, after emitting a series of ultrasonic pulses, a pattern of points of treated (destroyed)

tissue may be formed instead of a pattern of circles of treated tissue. A variety of mechanical means well known in the art may be employed to drive and control the motion of the transducer elements.

During treatment, the transducer 40 is applied to the patient. The transducer 40 might at any particular time, be wholly within, or outside of or, partially within the treatment region. The transducer 40 according to the principles of the present invention, may be manipulated by hand to move over two dimensional surface treatment area of the skin or in one dimension by means of an articulated arm or another mechanical device. Alternatively, the transducer may be manipulated with a motorized system. While motorized systems may be capable of manipulating transducers in contact with skin, safety systems must be designed to ensure the safety of the patient. Each beam 141 (FIG. 4C) of a transducer element 20 within the transducer 40 may be selectively and independently activated only when the transducer element is within the transducer area. As shown in FIG. 2, the selective activation may be achieved by providing an optical fiber 21 through the center of each transducer element 20. An optical circuit 23 sends two colors generated from two different color LEDs 26a and 26b down the optical fiber 21 along an optical signal 24a. The reflected light 24b is applied to separate optical detectors 25a and 25b. The treatment region within the contour is painted with a dye that absorbs one of the two colors and reflects the other. Based on the ratio of the signal of the reflected light at the two detectors, it may be determined whether or not the beam is within the treatment region.

A light emitting diode (LED) (not shown) is mounted on the top of the transducer over each beam. The LED receives its light power from the signal to the corresponding beam. Accordingly, the operator may watch as the transducer is dragged across a treatment boundary of a treatment region to verify that the beam is "off" outside the treatment region and "on" inside the treatment region.

The HIFU transducer supplies a predetermined amount of ultrasonic energy per unit distance traveled (not per unit time) for each treatment region. Accordingly, if the transducer stops or hesitates, the beams are shut off. Each transducer comprises a laser position sensor 42 that is used as a relative motion sensor, similar to those found in optical computer mice, which measures the relative motion of the transducer. The laser position sensor provides a signal that controls the duty cycle of each beam of the transducer elements. An indicator is included on an operator panel that shows a percentage of the maximum allowable speed at which the transducer speed is being dragged. If the transducer is dragged too fast, an operator alarm light will go on.

The HIFU transducer also comprises sensors that detect cavitation 43 and boiling of the fat tissue. The cavitation and boiling sensors verify that the system is operating correctly. The effectiveness of each beam within the transducer is determined by sequencing through and isolating the active beams at periodic intervals. The combination of the transducer and sensor in a single body is also referred to as the transducer assembly to avoid confusion with a treatment transducer for HIFU emissions, or an imaging transducer alone.

The HIFU transducer further comprises an ultrasonic A-trace sensor 45 that monitors a bottom of a fat layer within the treatment region. The bottom f the fat layer must be a safe distance below the effective bottom of the treatment zone. If it not, the beams of the transducer elements are shut down and an alarm light on the operator panel goes on.

The HIFU transducer comprises three or four redundant measurement and safety systems to avoid damaging the skin, muscle, or other organs. For example, as the HIFU transducer moves, the position measured by the relative motion sensors 42 will be correlated with and compared to the skin fingerprint to determine the position of the transducer relative to the skin fingerprint. Probes 43 and 44 are attached that measure the size and volume and distribution of the damaged tissue. Other probes 45 keep track of the fat thickness and compare it with that in the data file. The file is continuously updated to maintain high integrity data on each patient. The file also contains the treatment plan and the actual data taken from measurements of the various sensors. These sensors are generally include passive imaging methods for keeping track of the complex geometry of the treatment region. Separate data overlays are provided to characterize cavitated, boiled, and heated tissue within the treatment region. A display comprising the fusion of the data collected from the abovementioned sensors all information is provided to the practitioner carrying out the treatment plan. A safety shutdown occurs if any inconsistencies in data stored in the computer and data measured from the sensors occur.

Figure 4B:
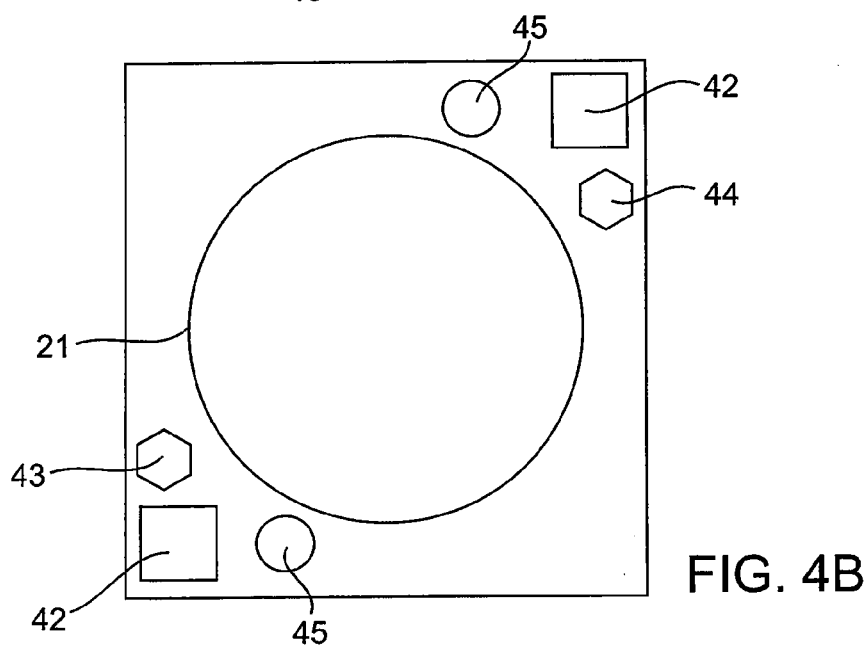
Figure 4C:
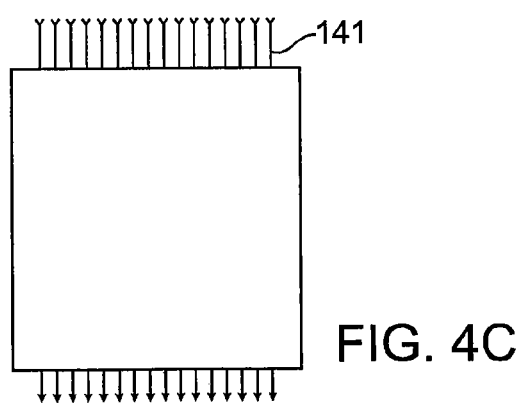

FIG. 4B illustrates an alternative embodiment with a single piezoelectric element in place of the 16 element array.

Reference will now be made in detail to the HIFU transducer in accordance with the principles of the present invention that is illustrated in the accompanying drawings.

As shown in FIG. 5A, a conventional HIFU transducer produces beams that have a tissue kill zone 51a along the beam axis near a focal point 22 of the transducer element. When conventional transducer elements are set for maximum destruction, this kill zone is about 2 mm in diameter and 18 mm long. There are many applications using fat destruction where the fat layer 29 is substantially less than 18 mm thick. As shown in FIG. 5B, and in accordance with the principles of the present invention, the length of the kill zone 51b is shortened using less power, less time, or using a shorter focal length transducer element. Accordingly, the rate of cell destruction decreases.

Contrary to conventional transducers that use multiple beams to compensate for the decrease in the rate of cell destruction, the transducers according to the principles of the present invention include piezoelectric elements with a mechanical modulator attached thereto which are generally formed from a Fresnel type lens. The mechanical modulator modulates an ultrasonic wave produced by the piezoelectric generator and focuses it into multiple beams. According to one embodiment of the present invention, the beams of the transducer are applied to the treatment region to create destroyed fat cells arranged in a hexagonal matrix pattern. Accordingly, the center-to-center spaces of treatment zones are arranged at about 0.5 mm to about 3.0 mm, depending on the depth below the skin surface to avoid a skin puckering phenomenon. It is noted that short focal length transducers produce lesions in the patient that have sub-millimeter spacing with a large number of beams, and deeper focal length transducers have fewer beams. The aforementioned arrangement of transducer elements, however, will provide a smooth skin surface. A smooth skin surface is obtained by creating a three dimensional spatial pattern of beams wherein the focal spots (overlapping beams behave as focal spots and possess acoustic intensities nearly as high as at the focal point, are well separated and wherein the transducer can be scanned to produce finely spaced cells). By creating the three dimensional spatial pattern beams, the deleterious effects of the presence of focal spots near the skin surface, and thus the skin puckering phenomenon, is avoided.

In one aspect of the present invention, the transducer system increases efficiency by emitting two or more beams at different frequencies to the same spot. One beam operates at a higher efficiency, creating a cavitation bubble and the second beam operates at lower frequency. Similarly additional beams also operate at different frequencies. The lower frequency beam is below optimum value, but takes advantage of the bubble created by the high efficiency beam. Accordingly during treatment, there is less absorption of ultrasonic energy in the skin than a single frequency transducer and the rate of tissue destruction in the fat increases.

The transducer elements within the HIFU transducer may be focused using a coupling plate formed of two materials to couple the transducer to the skin. The two materials have acoustic impedances that match that piezoelectric element to the skin. The two materials according to the principles of the present invention comprise aluminum and plastic.

Focusing the transducer elements to a point is achieved by creating an appropriate phase front at the face of the transducer. The phase shifting can be accomplished by changing the relative thickness of the aluminum and plastic and maintaining the sum of the two thicknesses at a constant. Accordingly, the coupling plate is a constant thickness. If another focal spot were desired, a different phase pattern is required.

Multiple focal spots may be modeled by calculating the phase at each element to achieve a focus point 1 (P1) and the phase for point 2 (P2). There is a theorem that states if two sine waves of the same frequency but different phases and amplitudes are added, the result is a sine wave of the same frequency and same phase and amplitude that can be calculated from the two given phases and amplitudes. A sine wave of this resultant phase applied to each element results in two focal spots. The theorem may be extended to any number of focal spots.

Using the abovementioned theorem, one can calculate a phase function that will simultaneously focus at two or more spots. These spots can be located arbitrarily, i.e., they need not be in line or even at the same distance from the transducer face.

Figure 6:
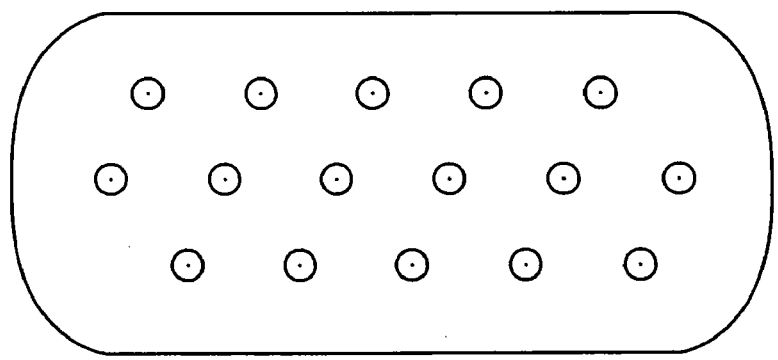
FIG. 6 illustrates a pattern of piezoelectric elements in a transducer assembly.
Figure 6A:
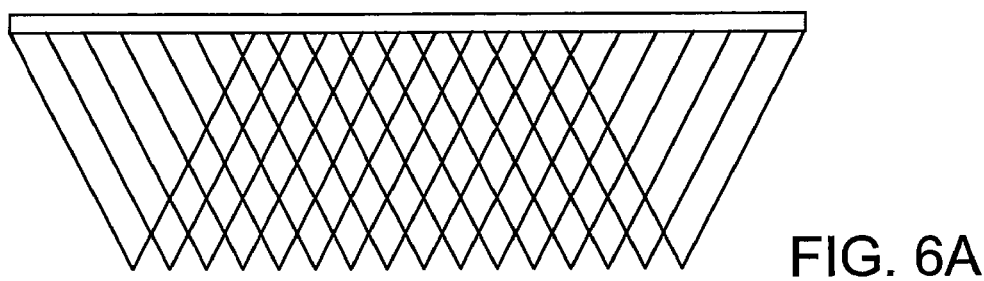
FIGS. 6A and 6B illustrate relationships between transducer elements and tissue destruction along a transducer scanning direction.
Figure 6B:
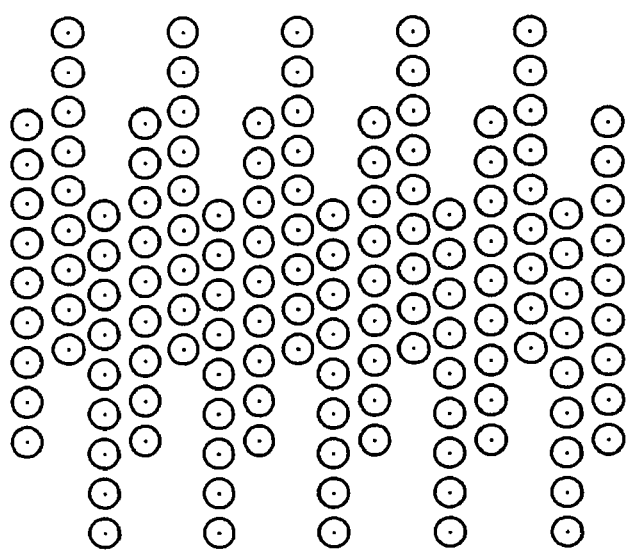

With reference to the pattern shown in FIGS. 6 and 6A, these aforementioned spots are located in a three dimensional "saw tooth" pattern. By scanning and/or pulsing the transducer, the resultant pattern of dead tissue would be in the hex pattern is shown in FIG. 6B. The pattern of dead tissue is much finer than the focal spot spacing. This scheme keeps the beams well separated where they penetrate the skin.

Figure 8:
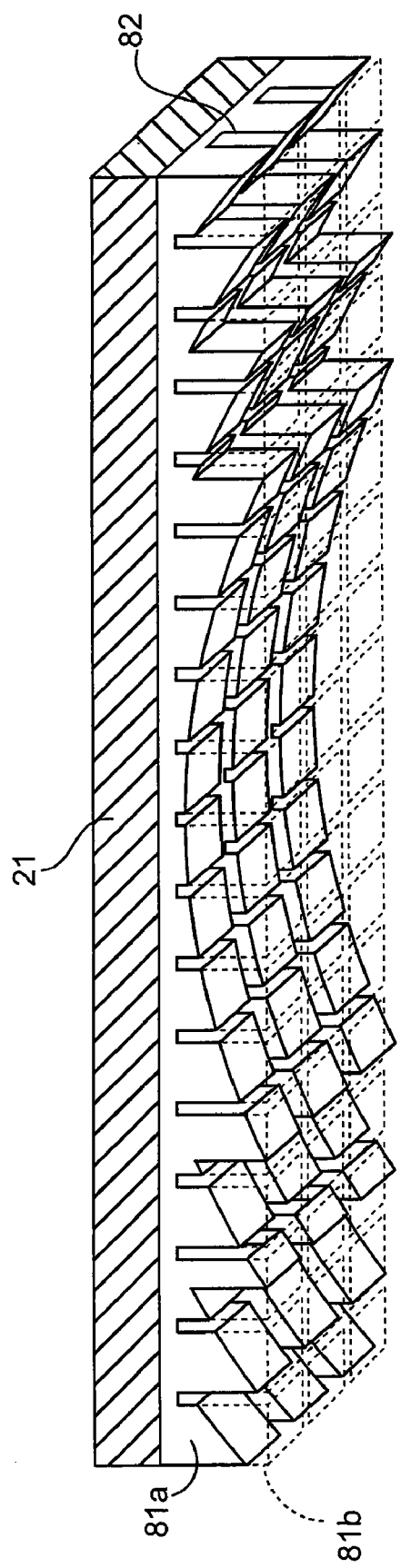

The mechanical modulator 70 for a single focus is depicted in FIG. 7. The mechanical modulator 70 includes the aluminum layer 71a coupled to the piezoelectric layer and the plastic layer 71b, coupled to the first matching layer. At locations where the phase reaches 360°, the phase is reset to 0°. The mechanical modulator of FIG. 7 can mask some of the wave as shown in the shadow regions 7. The wave masking affects only a small percentage of the total beam and therefore, does not affect focusing. The wave masking, however, does slightly decrease the efficiency of the wave. In order to compensate for the decrease in wave efficiency, the mechanical modulator is diced as shown in FIG. 8. The dicing creates, in effect, an "acoustic pipe" having analogous effects on vibration as a light pipe has on light. The phase modulation is then defined at the mechanical modulator surface rather than the aluminum-plastic interface. Accordingly, shadowing does not occur.

In a two-component (aluminum-plastic) system such as that shown in FIG. 8, the ratio that produces the desired phase at the surface produces a reflected wave, or reflected impedance, back into the transducer element. This creates a variation in "efficiency" across the face of the transducer. In the two-component system, the aluminum 81a is machined, then a plastic 81b is cast and then polished to be parallel to the back surface of the aluminum. This arrangement is then diced. The cuts 82 are centered at one-half wavelength (12 mils at 10 MHz) or less.

Alternatively, a three-component (aluminum-plastic (A) -plastic (B)) system may be designed that simultaneously provides the proper output phase and reflected impedance. The three-component system requires machining the aluminum, casting and machining plastic (A), and then casting and polishing plastic (B). Holding the tolerances in the three-component system, however, results in higher manufacturing costs.

Figure 15A:
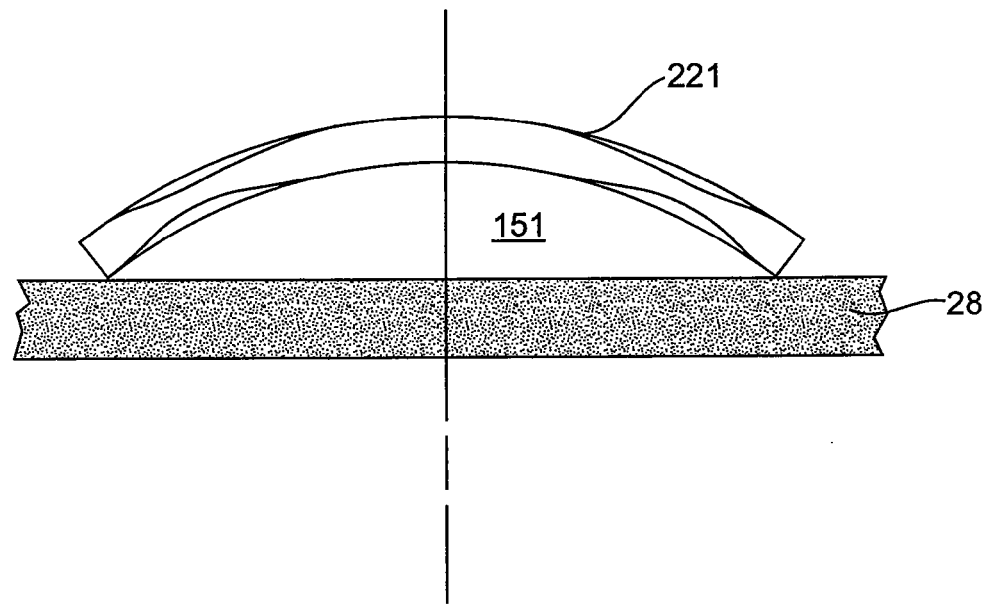
FIGS. 15A and 15B, 16, and 17 illustrate various transducer assemblies in accordance with the principles of the present invention.
Figure 15B:
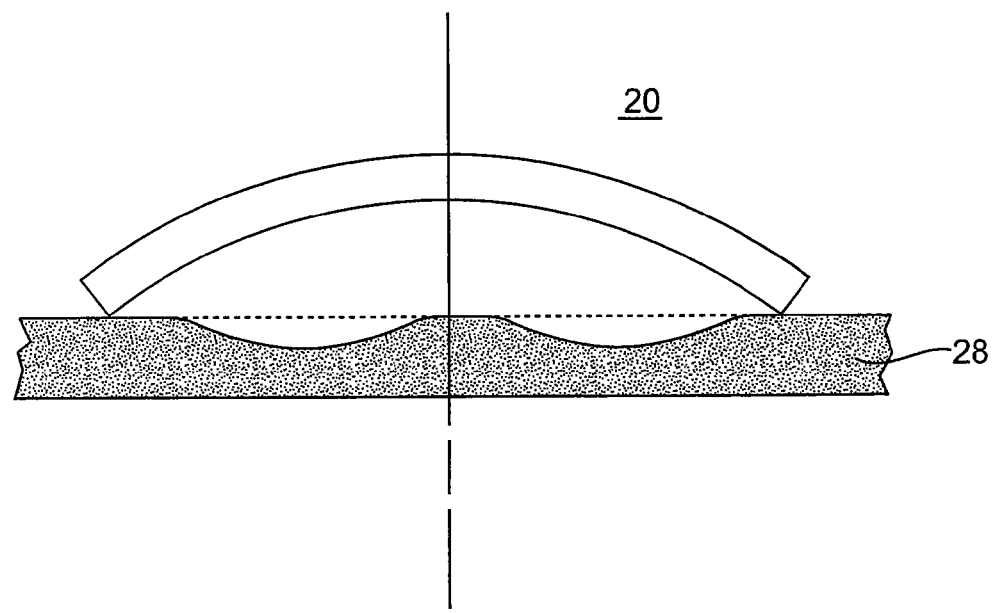
Figure 16:
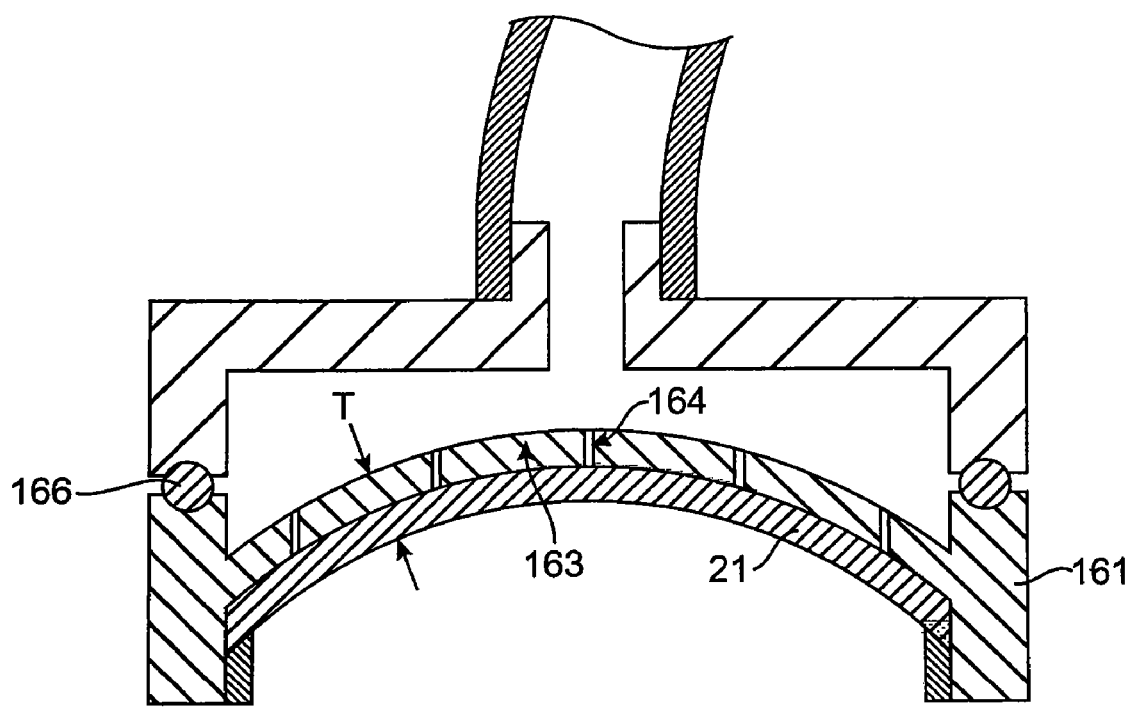
Figure 17:
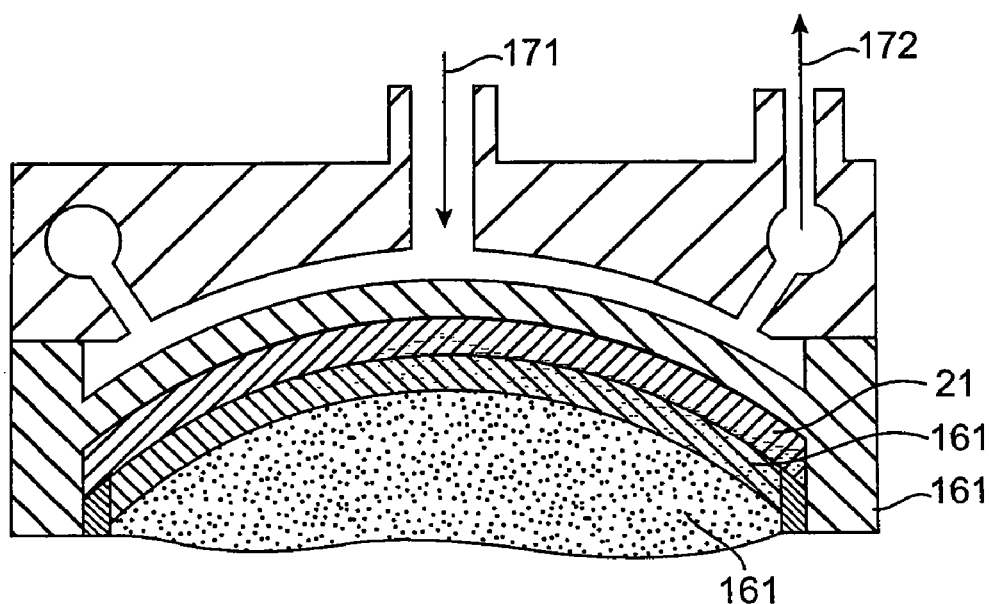

According to another aspect of the present invention, as generally shown in FIGS. 15A and 15B, the transducer elements 20 may comprise a simple spherical piezoelectric 21, made of a monocrystalline piezoelectric ceramic, with solid plastic 151 between the skin 28 and the piezoelectric. The solid state plastic 151 has a curved surface capable of focusing the phases of the waves from the piezoelectric to a single point. The transducer elements 20 according to the present embodiment may beneficially by made using existing tooling for the piezoelectric and fine corrections may be made to the solid after the transducer element is made. More specifically, and referring to FIG. 16, the transducer element includes a metal 161 with a lower expansion coefficient that the piezoelectric ceramic 21 and forms a back plate 163 having an antireflection thickness, T. Antireflection thickness T may be $n\lambda/2$, where n is any integer and $\lambda$ represents the wavelength of the wave. Small holes 164 are drilled to allow a vacuum 165 to pull the ceramic into place during assembly. O-rings 166 allow the metal 161 to couple to the vacuum when the vacuum is activated. The edge of the ceramic 21 butts against the metal. As the temperature increase, the ceramic undergoes compression. As shown in FIG. 17, the transducer element according to the present aspect of the invention is cooled by cool air 171 while hot air 172 is expelled out of the transducer element. Fins (not shown) may be mounted on the ceramic backing and the housing to channel air flow and increase heat transfer.

Knowing the location of the HIFU probe is critical. When the beam is turned on, it is essential that only fat be in the kill zone. It is also important from a cosmetic standpoint that the treatment be applied in a geometrically precise way.

The coordinate system is preferably not fixed to the treatment room of the treatment bed or other treatment device because the location of the patient moves relative to these coordinates on any predetermined treatment visit according to treatment plan. Even breathing can alter special fat coordinates. The best reference is the skin of the patient, to which the subcutaneous fat is attached.

Accordingly, there are four levels of measurement required in accordance with the principles of the present invention: 1) determine position from a reference point or line with the relative motion sensor; 2) determine position by counting grid lines placed on the skin; 3) determine position by using a grid with a position encoded on the grid; and 4) determine position by using imperfections in the skin as the reference, i.e., the skin fingerprint.

Determining the position of the transducer using the relative motion sensor is aided by the placement of a grid on the body of the patient. The relative motion sensor of the transducer is placed on a known grid point and moved to another to supply reference. In accordance with another exemplary embodiment, a "ball and socket" type relative motion sensor similar to a computer mouse with a mouse ball, but including a rotational sensor, determines the degree with which the ball within the socket has rotated of the sensor (and thus the degree to which the mouse has traveled) may be used instead.

Beneficially, the method includes the steps of using two longitudinal and transverse measurements with laser light provided at the top, bottom, left, and right positions of the HIFU transducer. Differential measurements may correspond to rotation. In accordance with another exemplary embodiment of the present invention, the laser position sensor may use a moving speckle pattern to detect motion, thus eliminating the need for the grid.

Alternatively, rather than keeping track of position only with the aforementioned mouse-type relative motion sensors, a grid may be drawn on the skin of the patient. The grid is drawn with a paint containing a pigment that is sensitive to a particular frequency of some laser light. Fiber optic sensors coupled through the transducer to the skin are then used to count grid crossings. There are many ways to distinguish x and y coordinate grids using differential lights, paints, etc.

Software controlling the operation of the transducer is programmed to expect grid crossings within some predetermined tolerance limit. If the crossings do not occur within those limits, ultrasonic energy within the transducer elements will shut off. If a positional error of some sort will have occurred, the ultrasonic energy within the transducer elements will be shut off. The practitioner then sorts out the problem and restarts the procedure at a known restart point.

When data is to be compared over many treatments the grid according to the principles of the present invention may still be reapplied at the same location. Reapplication of the grid may be accomplished, first of all, by realizing that the grid is not an orthogonal coordinate system projected on a planar surface, but is on a surface of a complex shape, i.e., a belly button.

After removing hair, a transparent photosensitive paint is applied to the body. The sensitivity is not as high as a transparent photographic emulsion and is sensitive to only one color, i.e., violet (the more energetic end of the visible spectrum). A camera scans the skin surface and records irregularities in 100 ms—a short enough period that patient motion is negligible. A resolution of 200 lines/inch should suffice. A 10×20 inch (25×50 cm) area requires 2,000×4,000 pixels. A second scan projects the grid to the skin surface. The grid is then developed and fixed. The fixing applies the grid to the skin surface so that the grid does not wash off, but wears off in a day or so. Alternatively, the grid may be removed by washing the grid off with a special solvent immediately after the treatment procedure.

The resultant grid provides the coordinates for storing the ultrasonic imaging data to get fat thickness as well as the treatment.

Upon return of the patient, the patient is painted and photographed again. The skin irregularities are cross-correlated to a previously formed image file and a warped gird is created and projected. The warping is done to project the grid to the same position on the skin as the previous grid. For example, current Pentium processors require perhaps 30 seconds for the cross correlations. There are, however, Xilinx chips with up to 800 multiplier/accumulate elements that can outperform the Pentium by a factor of 100 for fixed algorithms. This allows the warped grid to be calculated in about 30 ms—fast enough to project the grid before patient motion. This grid is fixed and the next treatment procedure is carried out.

In yet another alternative embodiment the position of the transducer is determined using a grid with a position encoded thereon. Accordingly, the grid in the present embodiment includes an absolute position encoded therein. The relative motion sensor is then adapted to sense position without measuring motion. The grid looks like orthogonal barcodes. A "thick" grid line represents a "1" and a "thin" grid line represents a "0". The grid lines are as close together as needed, for example 1 line/mm.

In another example of the encoded grid method, a pseudo-random sequence is used. At 1 mm spacing, 512 lines cover over 50×50 cm. Every group of nine consecutive lines provides a unique code. In other words, when the transducer moves 1 cm in both directions, the relative motion sensors pick up the transducers' absolute position. The probe then follows along the grid on an absolute basis.

In still another alternative embodiment, the position of the transducer is determined without the use of a grid. More specifically, and in as much as a standard NTSC television frame takes 33 ms and the cross-correlation takes 30 ms, the aforementioned grid may be eliminated altogether. Camera chips available at 0.5×0.5 inch are used in the present embodiment. The present invention contemplates mounting the camera chip in the transducer and coupled directly to the skin through the fiber optic faceplate. The skin is imaged at 1 mil resolution and a determination step observes whether each 0.5×0.5 inch square of the skin is unique when viewed at 1 mil×1 mil resolution. If it is not, a larger camera chip is used with a tapered fiber optics bundle and/or a local, rather than global, search for a relative motion sensor reference is based on motion from its last known location, e.g., 1/30 sec. ago.

Regardless of whether an actual grid is used on the skin or a fingerprint is used for location, a virtual grid is always created in the computer. This virtual grid provides the coordinates for all treatment records.

A grid with an area of 50 cm×50 cm at 0.2 mm resolution includes 6.25 million grid intersections. The aforementioned grid is more than adequate to store sonograms in three dimensions from 10 MHz ultrasonic B-scans of linear arrays.

The image survey is collected with one or two fiber optic cross-correlator systems, or grid sensor systems, at both ends of the imaging transducer. The echoes occur in a theoretical plane through the axis of the transducer face. This virtual grid is incommensurate with a rectangular grid, let alone a grid "attached" to the skin surface.

Prior to the present invention, there was no technology for monitoring HIFU lesions as they were created. There were some systems that ensonify with HIFU with a sequence of on and off times. Between ensonifications, an imaging system was then activated. The aforementioned prior art system provided an image a few seconds or longer after the lesion was created. Furthermore, there existed no technology to monitor the creation of multiple HIFU lesions if they were not in the same vertical plane.

Figure 9:
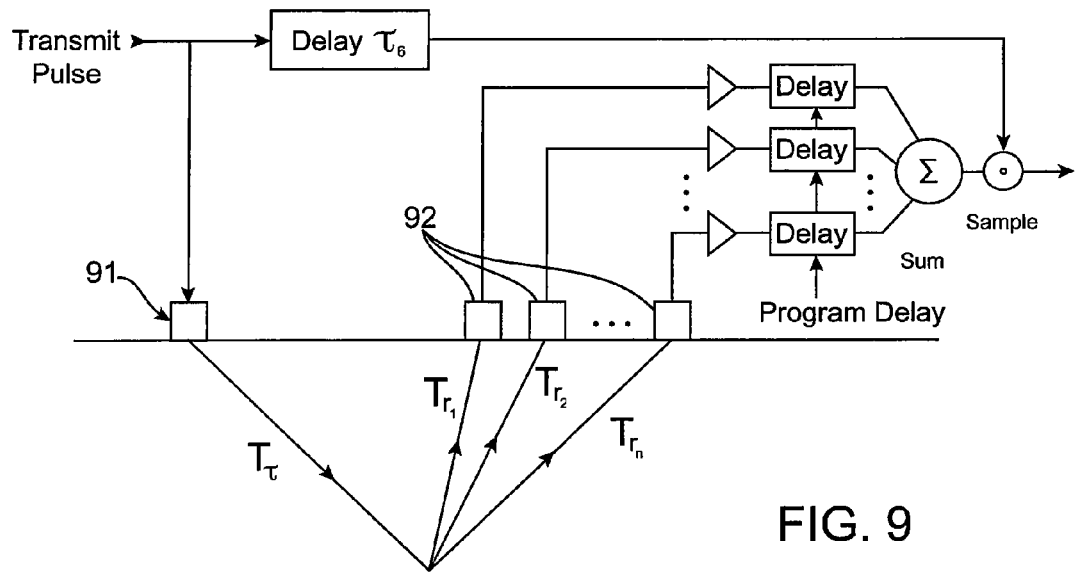
FIG. 9 illustrates a HIFU lesion imaging system.

The basis of conventional ultrasonic medical imaging arrays involves launching a pulse of controlled shape into the tissue, then detecting and processing the echoes. As shown, conventionally, in FIG. 9, a pulse is transmitted using some element and received by others, which may include the transmitting element 91. To find the grayscale at any x-y location, i.e., at any pixel, the delay time, $T_{dl}$, of each receiving element 92 is set so that $T_t+T_n+T_{dl}=T_c$, where $T_t$ is the transmitting time and $T_n$ is a receiving time, a constant for that pixel. Then sample the sum of all received signals at that time $T_c$. The grayscale for that pixel is monotonically related to the absolute value of the voltage. There are many variations in the details of how this process is done and they are well known to practitioners in the art. All of these variations involve using the time of travel of a pulse of known form from the transmitting element or elements to a pixel, then from the pixel to the receiving elements to determine if an echo is scattered from that pixel.

In accordance with the principles of the present invention, however, sound created by the lesion is used to either monitor lesion creation or to image lesion creation so that the HIFU dose may be controlled. The present invention allows multiple lesions to be independently monitored and imaged.

This present invention produces an image from sound created at the pixel location. The sound need not be a pulse or be of any particular form, i.e., the sound may be incoherent. In the present invention, the sound may originate from the collapse of a cavitation bubble or from boiling fluid created near the focus of a HIFU beam. The present invention does not look for the change in tissue scatter characteristics created by the HIFU system, but rather for the HIFU process itself.

Additionally, using ultrasonic Doppler techniques, the present invention is capable of monitoring the growth of cavitation bubbles or the turbulence caused by the boiling fluid for use in determining the how power is applied to the transducer during the HIFU process, as will be described in greater detail below.

Figure 10:
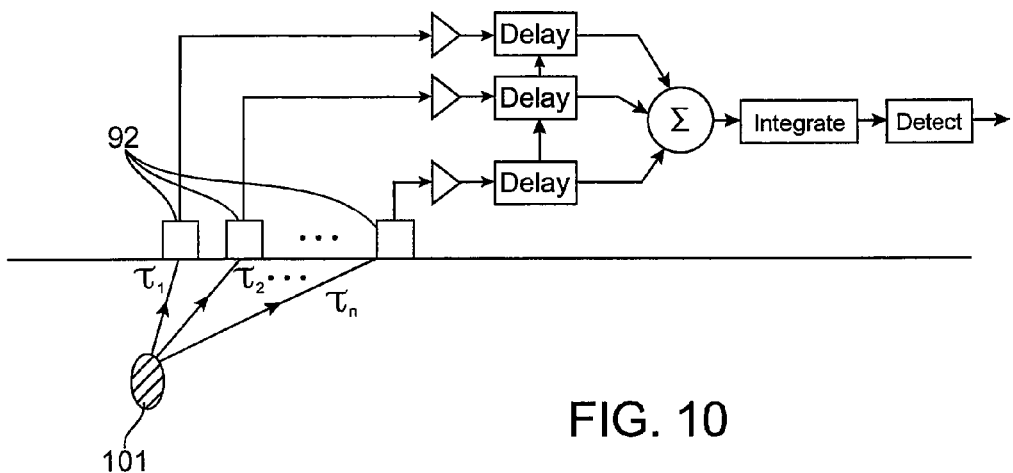
FIG. 10 illustrates a HIFU lesion imaging system in accordance with the principles of the present invention.

The imaging system according to the principles of the present invention is illustrated in FIG. 10. The presence of a sound generator 101, i.e., cavitation or boiling activity, is determined at pixel location P, by setting the delays such that the signals $T_n+T_{di}=T_c$, a constant time for that pixel. The signals are summed and detected using their RMS value. This detected signal is then averaged over some arbitrary time period using a low-pass filter or integrator. The output voltage represents the sound being generated at the pixel. If there is sound from some other location, the signals going into the summing machine are of a random phase. Random phase signals include signals having, at any instant, some voltages being positive, some negative, and, on average, zero.

Three types of sound that may be detected from a pixel created by HIFU include: scatter from HIFU ensonification, cavitation, and boiling. The HIFU ensonification is at some frequency, f. Sometimes there is some energy at harmonics of this, i.e., frequencies of nf, where n is an integer. Cavitation sounds occur at subharmonics, i.e., f/n. Boiling creates sounds over a broad spectrum. These are illustrated in the spectrum shown in FIG. 11. FIG. 12 illustrates how this signal can be broken into three channels. Accordingly, all three sounds can be processed in an image. The present invention is concerned more towards cavitation and boiling. Accordingly, high pass output associated with HIFU ensonification will be ignored.

The HIFU transducer is surrounded with a circular or rectangular array, depending on the HIFU transducer shape, of receiving elements. If sound were created somewhere in fat tissue, that wave would arrive at each element, except at different time, depending on the distance between the transducer and the receiving elements. Adding delay lines to each element aligns all received signals from a particular pixel in time and adding them determines the amplitude. If the sound is from a particular treatment point, then the amplitude is large, but if the sound is from some other point, the phases will be random and the amplitude is small. The fundamental difference between this and pulse-echo ultrasonics is that, in pulse-echo systems, the signal from each piezo element of a transducer is sampled at one time for each pixel, whereas in the present invention, the data for each pixel is collected continuously at each element. Accordingly, several hundred receiving elements are needed. If 300 were needed, then 300 delay lines would be needed for each. If the image were made in the focal plane of the HIFU transducer, there might be 300×300 pixels. This results in 27 million delay line taps. Furthermore, images must be made in planes above and below the focal point.

Taking advantage of the fact that, if many signals of the same frequency but different amplitudes and phases are added, the sum is a signal at the same frequency with some resultant amplitude and phase the present invention may be practiced. In particular, $\Sigma_i A_i \sin(\omega \tau + \theta_i) = B \sin(\omega \tau + \theta)$ Where $B^2 = (\Sigma_i A_i \cos \theta_i)^2 + (\Sigma_i A_i \sin \theta_i)2$ And $\theta = \tan^{-1}((\Sigma_i A_i \sin \theta_i)/(\Sigma_i A_i \cos \theta_i))$ The phase and amplitude can be directly determined for each transducer from the sine ($s_i$) and the cosine ($c_i$) component of the Fourier transform. In particular, $\theta_i = \tan^{-1}(s_i/c_i)$ and $A_i^2 = c_i^2 + s_i^2$ The time shift is accomplished by adding a constant to the phase.

Figure 11:
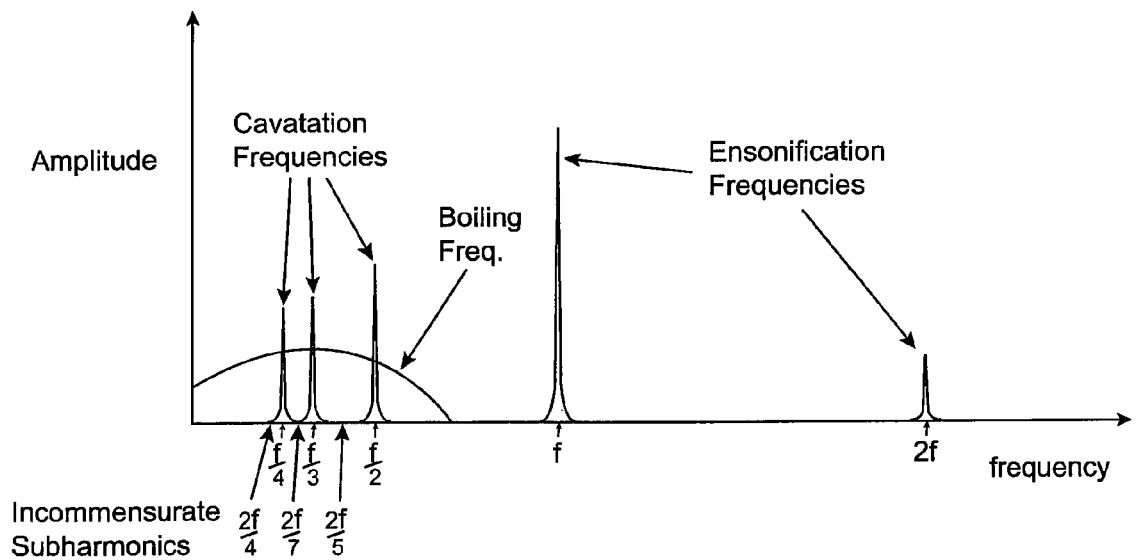
FIG. 11 illustrates the relative frequency/amplitude relationships between cavitation frequencies, boiling frequencies, and ensonification frequencies.
Figure 12:
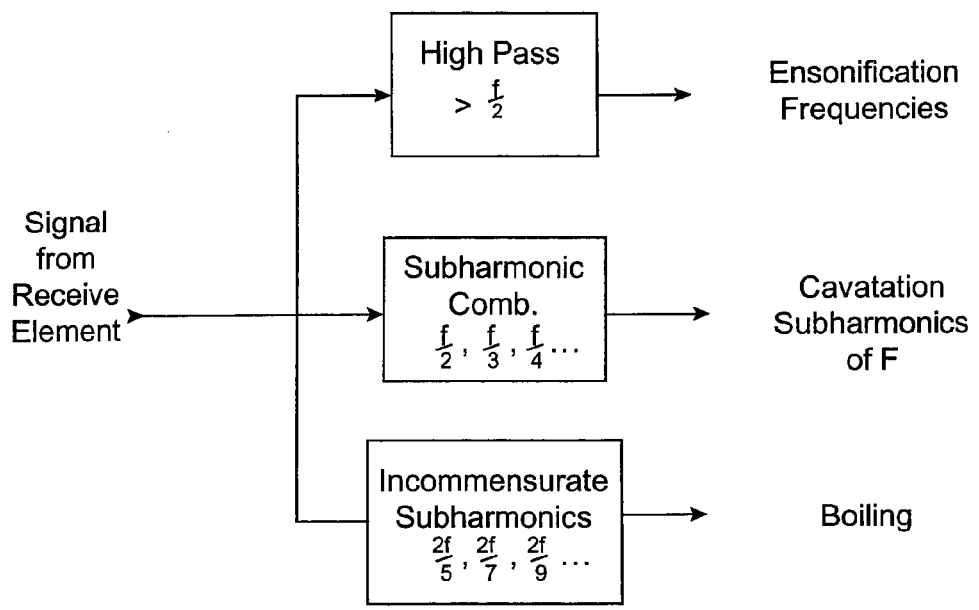
FIG. 12 illustrates signals received from receiving elements broken up for analysis.
Figure 13:
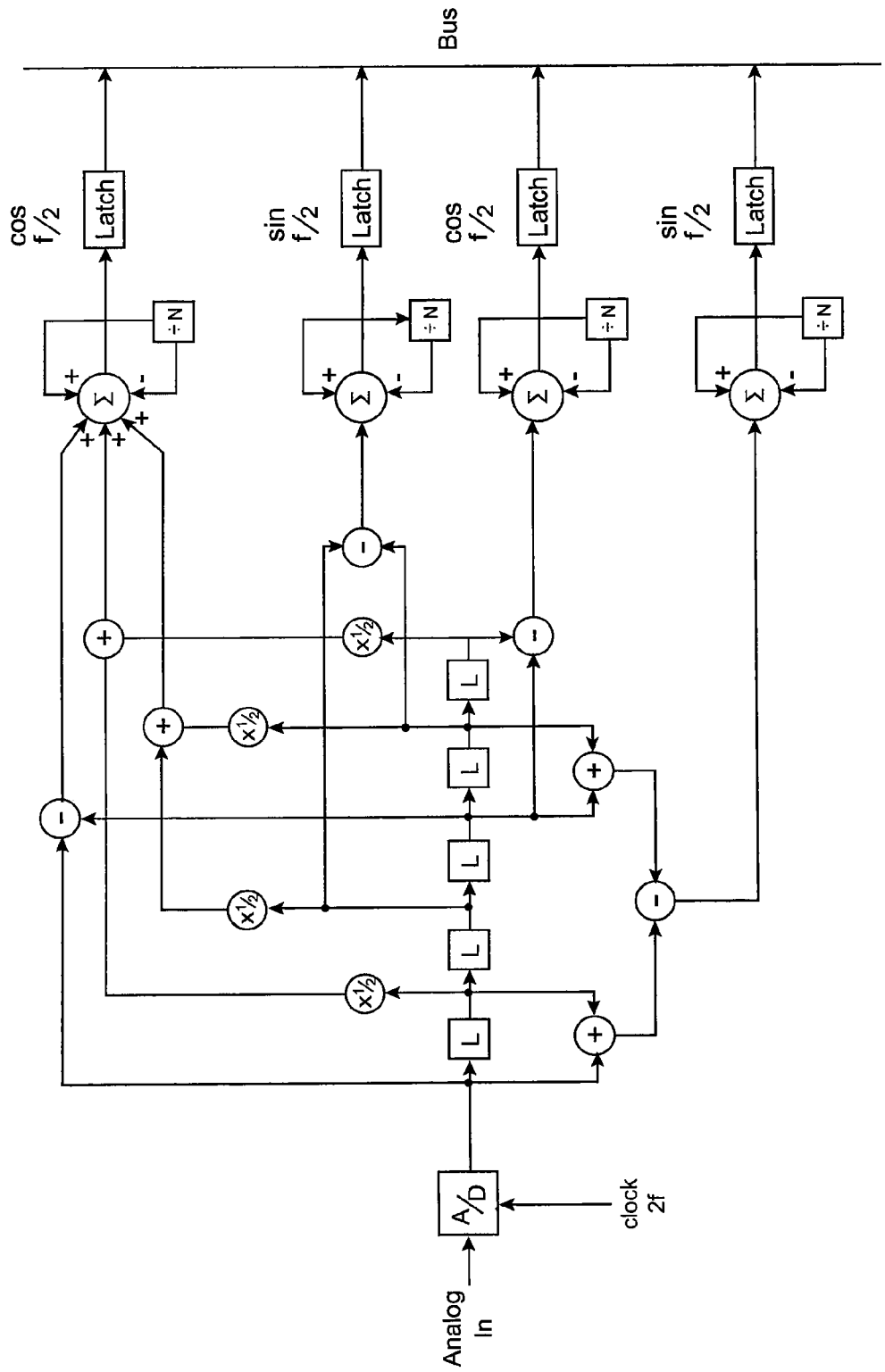
FIG. 13 illustrates a schematic view of digitizers configured to extract transformed frequencies.

When considering sound caused by cavitation, FIG. 11 shows that the spectrum contains f/2 and f/3 frequencies. These two spectrums are used to form two images. The received signals are digitized at twice the HIFU frequency. Digitizers are available at about $1.50/channel, so 300 digitizers would cost $450.00. As shown in FIG. 13, the digitizers are then processed through delay lines that are hardwired to extract the sine and cosine transform at f/2 and f/3 frequencies. A minimum of 8 taps are required, but more provide a narrower spectrum and slow the output rate. The output rate is the digitization rate 2 f divided by the number of shifts. For example, if the HIFU frequency were 6 MHz, the signal would be sampled at 12 MHz and, with the minimum of 8 taps, the transform would be calculated at 1.5 MHz. Since there are two frequencies each with a sine and cosine transform, this provides 6 Ms/s (mega samples per second). If the number of taps were increased to 64, this results in 750 ks/s. This may still be too much to process into an image. Thus an accumulator is added after the transform to accumulate successive transforms. It is assumed that the cavitation bubble does not grow or disappear to fast. A 64 tap FET occurs in a 5.3 microsecond at 6 MHz, so an accumulation of 64 still takes only 0.3 ms. This represents 2 meters of signal flow so that the difference in arrival time (a few cm) between elements is small compared to this. Put another way, the fact that the time delay of the cavitation noise to each element from one pixel is different can be ignored because the signal is being averaged over a time interval of about 100 times the difference.

Producing 10 image planes, each consisting of 100×100 pixel images at 2 frequencies, using a 200 element array at a rate of 10 frames/sec requires adding the phases of the signals at a rate of 0.8 Gs/second using a DSP (digital signal processor). Alternatively, a chip may be configured for this specific task to be about 100 times faster than the previously mentioned DSP. Thus, more pixels, more planes, or faster frame rates are all feasible.

When considering sound caused by boiling, different from considering sound caused by cavitation where the phase of the cavitation was locked to the HIFU frequency and the received signal changed phase only because of the growth of the bubble, frequencies produced by boiling are independent of the HIFU drive frequency. In fact, sounds produced by boiling persist after HIFU ensonification stops. Accordingly, it is not clear that the phase produced by boiling remains stationary for the 20 microsecond difference that the signal takes to travel from a close transducer element to a far one.

Another characteristic of noise from boiling is that it cannot be turned on and off as quickly as cavitation. Thus, a few frames of images per second, as used in considering cavitation, is not fast enough.

Accordingly, the present embodiment of the invention picks frequencies from the hardwired Fourier transform that are incommensurate with the subharmonics. These are monitored for some period of time, for example, 4 samples at 1.5 microsecond intervals. A curve is then put through these to estimate the phase at any particular time. Thus, the difference due to path length differences from pixel locations to the various piezo elements can be taken into account. The processing is similar to that shown in FIG. 13 except that: 1) the Fourier frequencies are incommensurate with the subharmonics of HIFU; 2) the transforms are short because the phase may be moving too quickly for long transforms; 3) four, rather than one, transforms are stored for analysis; and 4) the phase for the sum is obtained by interpolation rather than adding.

In accordance with one aspect of the invention, the monitored Doppler dynamic sound caused by cavitation or boiling may be used as an indicator to set a power level outputted by the transducer in the HIFU system to destroy fat tissue. Accordingly, the maximum power level applied to a transducer may be automatically determined for any given density of material. Thus, the total power used per treatment may be conserved and the lifetime of the transducer may be extended.

Operating power of HIFU transducers will now be discussed. HIFU transducers are rarely operated at their maximum power. This maximum is set by the maximum drive voltage, above which arcing occurs. Operating HIFU transducers this maximum drive voltage continuously results in the overheating and the destruction of the HIFU transducer.

In the conventional art, a transducer is operated with an on/off cycle to promote cooling, such as 1 second on and 4 seconds off. Even when it is on, the transducer is operated below the maximum power. In the example above, the average power is 20% of the peak. Transducers are not operated at the average power continuously because the biological effect of such an operation is nonlinear. A time/power threshold is needed to start cavitation, so there is more biological damage because of the higher peak power at the same average power.

Based on this principle that "if a little is good, a lot is better," the present invention operates the transducer at a higher peak power while maintaining the same average power to more efficiently destroy tissue. Accordingly, the maximum peak power may be used as much as possible. Ultrasonic energy is stored in a mechanical assembly and exits the transducer as a very high amplitude impulse such that the transducer delivers much more than peak power defined by the maximum peak voltage (or power) applied to the piezoelectric to increase the rate of tissue destruction. By maximizing the power exiting the transducer during the "on" interval in each on/off transducer operation cycle (ratios that are microseconds in duration) is operated at maximum power, heat generation in the transducer element does not conduct away in the interval and the advantage is the non-linear relationship between instantaneous power and tissue destruction.

Figure 14:
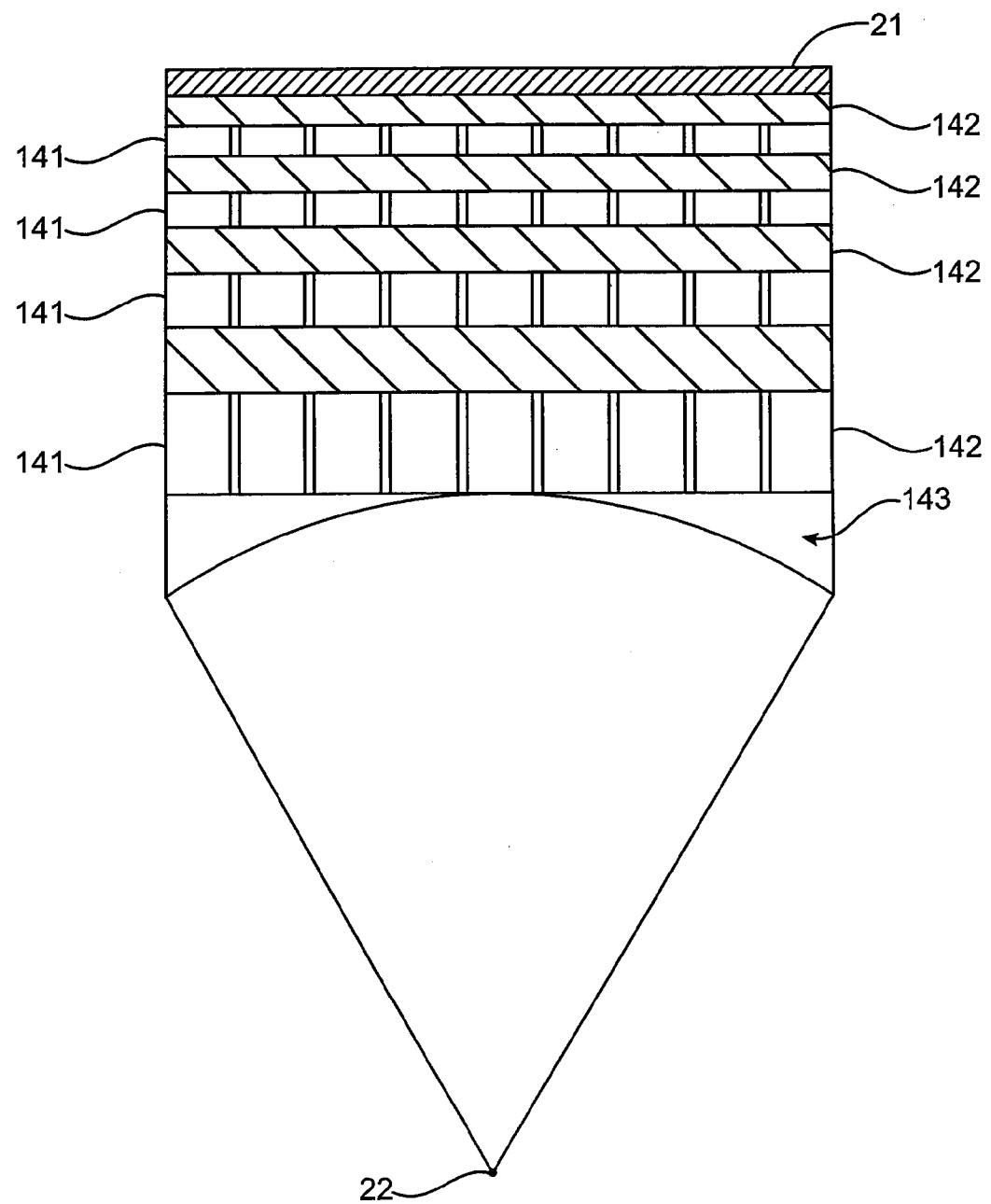
FIG. 14 illustrates transducer elements in accordance with the principles of the present invention.

As shown in FIG. 14, the transducer element of the present invention comprises a piezoelectric element with alternating lamina of high and low impedance 142 and 141, respectively, attached thereto. By transmitting a pulse into this assembly from a piezo element, the output would ring, and the peak intensity generated by the piezoelectric would result in a much lower peak power exiting. Accordingly, the present invention comprises transmitting a pulse into the assembly and recording the exit pulse at the focus. Then, the transducer is fed the exit pulse in a time-reversed format to allow a very high amplitude impulse to exit the assembly.

For example, a full power impulse is applied to the transducer and a ringing signal exits the assembly with a peak power of only 10% of the impulse. The ringing signal is then recorded digitally and played in reverse order using a digital to analog converter to generate a signal. The signal is then applied to the transducer at the peak intensity allowed by arcing criteria. The output pulse would then have a peak power of 10× the peak power initially applied by the transducer.

In accordance with one aspect of the present invention, application of reduced power level, subsequent to the application of the peak power level to the transducer, may be triggered by sounds generated by the HIFU system that are indicative of the onset of cavitation. Acoustic signatures indicative of the onset of cavitation or boiling may be determined using Doppler imaging techniques. Accordingly, the lifetime of the transducer may be extended by reducing the amount of time the transducer is operated at peak power, in an automatic fashion for any given density of material being treated.

It will be apparent to those skilled in the art that various modifications and variations can be made in the present invention without departing from the spirit and scope of the invention. Thus, it is intended that the present invention cover the modifications and variations of this invention provided they come within the scope of the appended claims and their equivalents.

What is claimed is:

1. An imaging system for use with an ultrasound system, the imaging system comprising:
    a high intensity focused ultrasound (HIFU) transducer having a plurality of transducer elements for treatment of a volume of living tissue;
    a video display having an X-Y coordinate display, the display having a plurality of pixels wherein each pixel has an X-Y address; and
    a controller configured to power said HIFU transducer, said controller having a video output configured to produce the X-Y coordinate display on the video display and a receive path configured to detect acoustic information from said volume of living tissue, the receive path comprising:
    a first receive channel configured to detect boiling by analyzing broad spectrum acoustic interaction radiating from said volume of living tissue; and
    a second receive channel separate from the first receive channel configured to detect cavitation by analyzing sub-harmonic frequencies (f/n) radiating from said volume of living tissue;
    wherein the video output is further configured to simultaneously provide a visual representation of boiling and a visual representation of cavitation if present at any particular pixel on the video display based upon detecting boiling and cavitation via the first and second receive channels.

* * * * *